United States Patent [19]
Jacobsen et al.

[11] Patent Number: 5,559,106
[45] Date of Patent: Sep. 24, 1996

[54] HETEROCYCLIC COMPOUNDS, THEIR USE AND PREPARATION

[75] Inventors: Poul Jacobsen, Slangerup; Flemming E. Nielsen; Lone Jeppesen, both of Virum, all of Denmark

[73] Assignee: Novo Nordisk A/S, Bagsvaerd, Denmark

[21] Appl. No.: 350,744

[22] Filed: Dec. 7, 1994

Related U.S. Application Data

[63] Continuation of Ser. No. 202,524, Feb. 28, 1994, abandoned.

[30] Foreign Application Priority Data

Mar. 19, 1993 [DK] Denmark ................... 0310/93

[51] Int. Cl.⁶ .............. C07D 487/04; A61K 31/495; A61K 31/675; C07F 9/6524
[52] U.S. Cl. .............. 514/81; 514/250; 544/337; 544/343; 544/346; 544/354; 544/356; 560/21; 564/428
[58] Field of Search ................... 544/337, 343, 544/346; 514/81, 250

[56] References Cited

U.S. PATENT DOCUMENTS 4,354,027  10/1982  Loev et al. ............... 544/346

OTHER PUBLICATIONS

McQuaid et al., J. Med. Chem., vol. 35, pp. 3319–3324 (1992).

*Primary Examiner*—Emily Bernhardt
*Attorney, Agent, or Firm*—Steve T. Zelson, Esq.; Elias J. Lambiris, Esq

[57] ABSTRACT

Quinoxaline compounds of the general formula

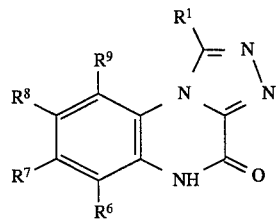

wherein $R^1$ is COX', POX'X" or alkyl substituted with COX' or POX'X", and X' and X" independently are hydroxy or alkoxy, and $R^6$, $R^7$, $R^8$ and $R^9$ independently are hydrogen, alkyl, halogen, $NH_2$, $NO_2$, CN, $CF_3$, $SO_2NY'Y"$ or COZ' wherein Z' is NY'Y" or alkyl and Y' and Y" independently are hydrogen or alkyl, triazolyl, imidazolyl, imidazolyl substituted with phenyl or alkyl, or $R^6$ and $R^7$, or $R^8$ and $R^9$, together form a further fused ring, are useful in the treatment of indications caused by hyperactivity of the excitatory neurotransmitters.

25 Claims, No Drawings

HETEROCYCLIC COMPOUNDS, THEIR USE AND PREPARATION

This application is a continuation application of application Ser. No. 08/202,524, filed Feb. 28, 1994, now abandoned, the contents of which are incorporated herein by reference.

The present invention relates to therapeutically active heterocyclic compounds, a method of preparing the same, pharmaceutical compositions comprising the compounds, and a method of treating therewith.

L-glutamic acid, L-aspartic acid and a number of other closely related amino acids have in common the ability to activate neurons in the central nervous system (CNS). Biochemical, electrophysiological and pharmacological studies have substantiated this and demonstrated that acidic amino acids are transmitters for the vast majority of excitatory neurons in the mammalian CNS.

Interaction with glutamic acid mediated neurotransmission is considered a useful approach in the treatment of neurological and psychiatric diseases. Thus, known antagonists of excitatory amino acids have shown potent anxiolytic (Stephens et al., Psychopharmacology 90, 143–147, 1985), anticonvulsant (Croucher et al., Science 216, 899–901, 1982) and muscle relaxant properties (Turski et al., Neurosci. Lett. 53, 321–326, 1985).

It has been suggested that accumulation of extracellular excitatory amino acids, followed by overstimulation of neurons, may explain the neuronal degenerations seen in neurological disorders such as amyotrophic lateral sclerosis, Parkinsonism, Alzheimer's disease, Huntington's disease, epilepsy, and deficiencies of mental and motor performance seen after conditions of brain ischemia, anoxia and hypoglycemia or head and spinal cord trauma (McGeer et al., Nature 263, 517–519, 1976; Simon et al., Science 226, 850–852, 1984; Wieloch, Science 230, 681–683, 1985; Faden et al., Science 244, 798–800, 1989; Turski et al., Nature 349, 414–418, 1991). Other possible indications are psychosis, muscle rigidity, emesis and analgesia.

Excitatory amino acids exert their actions via specific receptors located postsynaptically or presynaptically. Such receptors are at present conveniently subdivided into three groups bases on electrophysiological and neurochemical evidence: 1 the NMDA (N-methyl-D-aspartate) receptors, 2 the AMPA receptors, and 3 the kainate receptors. L-glutamic acid and L-aspartic acid probably activate all the above types of excitatory amino acid receptors and possibly other types as well.

The above mentioned classification of excitatory amino acid receptors into NMDA, AMPA, and kainate receptors is based primarily on the following electrophysiological and neurochemical findings.

1) N-methyl-D-aspartate (NMDA) receptors exhibit high selectivity for the excitant NMDA. Ibotenic acid, L-homocysteic acid, D-glutamic acid and trans-2,3-piperidine dicarboxylic acid (trans-2,3-PDA) exert a strong to moderate agonist activity on these receptors. The most potent and selective antagonists are the D-isomers of the 2-amino-5-phosphonocarboxylic acids, e.g. 2-amino-5-phosphono-valeric acid (D-APV) and 3-[(±)-2-carboxypiperazin-4-yl]-propyl-1-phosphonic acid (CPP), while moderate antagonist activity is shown by the D-isomers of long chain 2-amino dicarboxylic acids (e.g. D-2-amino-adipic acid) and long chain diaminodicarboxylic acids (e.g. diaminopimelic acid). The NMDA-induced synaptical responses have been extensively investigated in the mammalian CNS, especially in the spinal cord (J. Davies et al., J. Physiol. 297, 621–635, 1979) and the responses have been shown to be strongly inhibited by $Mg^{2+}$.

2) AMPA receptors are activated selectively by AMPA (2-amino-3-hydroxy-5-methyl-4-isoxazolepropionic acid), other potent agonists being quisqualic acid and L-glutamic acid. Glutamic acid diethyl ester (GDEE) is a selective but very weak antagonist of this site. AMPA receptors are relatively insensitive to $Mg^{2+}$.

Glutamate release has long been thought to play a major role in neuronal death resulting from cerebral ischemia (Benveniste, H. et al., J. Neurochem. 43, 1369–1374, 1984). It is well known that NMDA receptor evoked $Ca^{2+}$ influx is an important mechanism in ischemic neuronal cell loss. The non-NMDA receptor coupled ionophor is not permeable to calcium. However, the excitation by the Scaffer collaterals in the CA1 region is exerted by non-NMDA receptors, and this fact is of importance for the events in the postischemic period. Recent studies have shown that selective AMPA antagonists have neuroprotectant effects in global ischemia in the gerbil even when given several hours after reperfusion (Sheardown et al., Science 247, 571–574, 1990).

AMPA antagonists are therefore useful in the treatment of cerebral ischemia.

3) Kainate receptors. Excitatory responses to kainic acid are relatively insensitive to antagonism by NMDA-antagonists and by GDEE, and it has been proposed that kainic acid activates a third subclass of acidic amino acid receptor. Certain lactonized derivatives of kainic acid are selective antagonists (O. Goldberg et al., Neurosci. Lett. 23, 187–191, 1981) and the dipeptide 3-glutamyl-glycine also shows some selectivity for kainate receptors. $Ca^{2+}$ but not $Mg^{2+}$ is a strong inhibitor of kainic acid binding.

The affinity of a substance for one or more of the different types of excitatory amino acid receptors may be studied in simple binding experiments. In essence, the method involves incubation of a particular selected radiolabelled ligand and the particular specific substance to be investigated with brain homogenate which contains the receptor. Measurement of receptor occupancy is made by determination of the radioactivity bound to the homogenate and subtraction of non-specific binding.

AMPA receptor binding may be studied by using $^3$H-AMPA as radioligand.

The influence of glutamic acid analogues on secondary effects of glutamate receptor interactions may be studied in vitro by using the phenomenon of spreading depression in chicken retina. Such experiments will provide information as to the efficacies (agonist/antagonist) of the test substances. This is in contrast to binding studies, which only provide information on the affinities of the compounds for the receptor.

It has now been found that the compounds of the invention have affinity for the AMPA receptors and are antagonists in connection with this type of receptor which makes them useful in the treatment of any of the numerous indications caused by hyperactivity of excitatory amino acids.

The compounds of the invention are represented by the general formula I

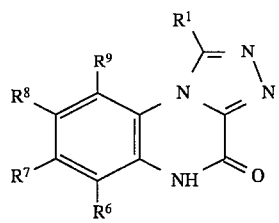 (I)

wherein

R¹ is COX', POX'X" or straight or branched $C_{1-6}$-alkyl substituted with COX' or POX'X", and X' and X" independently are hydroxy or $C_{1-6}$-alkoxy, and R⁶, R⁷, R⁸, and R⁹ independently are hydrogen, $C_{1-6}$-alkyl, halogen, $NH_2$, $NO_2$, CN, $CF_3$, $SO_2NY'Y"$ or COZ' wherein Z' is NY'Y" or $C_{1-6}$-alkyl, and Y' and Y" independently are hydrogen or $C_{1-6}$-alkyl, triazolyl, imidazolyl, imidazolyl substituted with phenyl or $C_{1-6}$-alkyl, or R⁶ and R⁷, or R⁸ and R⁹, together form a further fused ring;

or pharmaceutically acceptable salts thereof.

When R⁶ and R⁷, or R⁸ and R⁹, together form a further fused ring, the fused ring is preferably a benzo ring, a tetrahydro-benzo ring, a pyrido ring, a pyrimidino ring or a pyrano ring.

The invention also relates to a method of preparing the above mentioned compounds. The present compounds of formula I are prepared by a) alkylating a compound having the formula II

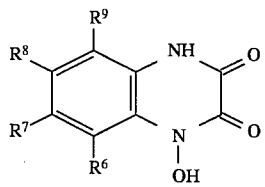 (II)

wherein R⁶, R⁷, R⁸ and R⁹ have the meanings defined above with benzylhalogenide to form a compound of the formula III

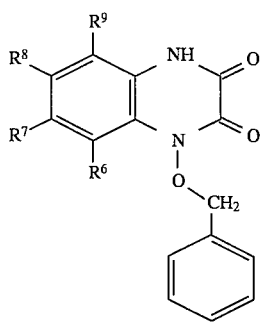 (III)

wherein R⁶, R⁷, R⁸ and R⁹ have the meanings defined above, and halogenating the compound to form a compound of the formula IV

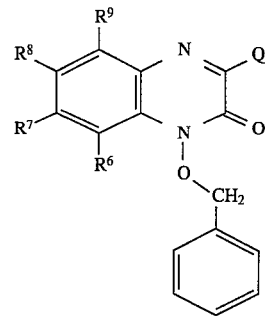 (IV)

wherein R⁶, R⁷, R⁸ and R⁹ have the meanings defined above and Q is Br, Cl, or I; and reacting the compound with hydrazine to form a compound of the formula V

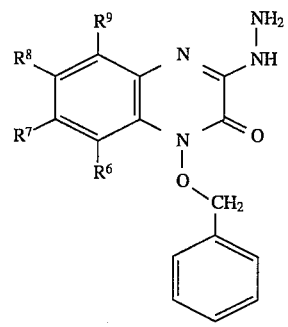 (V)

wherein R⁶, R⁷, R⁸ and R⁹ have the meanings defined above, and acylating the compound with an acylchloride with the general formula VI R¹—COCl    (VI)

wherein R¹ has the meaning as defined above for a compound of the general formula I wherein X' and X" are $C_{1-6}$-alkoxy to form a compound of the formula VII

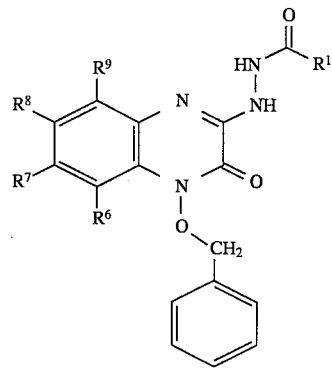 (VII)

wherein R⁶, R⁷, R⁸ and R⁹ have the meanings defined above, and hydrogenolysis of the compound to form a compound of the formula VIII

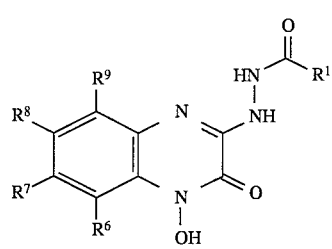 (VIII)

wherein $R^6$, $R^7$, $R^8$ and $R^9$ have the meanings defined above, and followed by thermal cyclization and simultaneous deoxygenation to form a compound of formula I, wherein X' and X" are $C_{1-6}$-alkoxy, or b) reacting a compound having the formula IX

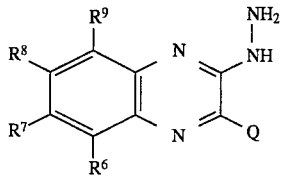  (IX)

wherein $R^6$, $R^7$, $R^8$ and $R^9$ have the meanings defined above, and Q is Br, Cl, or I, with a compound of the general formula VI

  (VI)

wherein $R^1$ has the meaning as defined above for a compound of the general formula I wherein X' and X" are $C_{1-6}$-alkoxy to form a compound of the formula XI

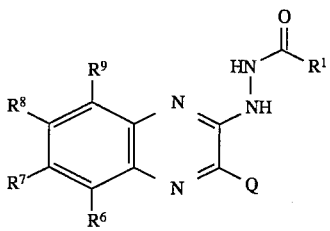  (XI)

wherein $R^6$, $R^7$, $R^8$ and $R^9$ have the meanings defined above, and Q is Br, Cl, or I, and then either cyclization followed by hydrolysis or simultaneous cyclization and hydrolysis to form a compound of formula I, wherein X' and X" are $C_{1-6}$-alkoxy, or c) substituting a compound of the formula XII

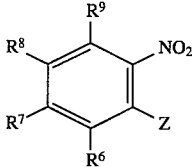  (XII)

wherein $R^6$, $R^7$, $R^8$ and $R^9$ have the meanings defined above and Z is either halogen or $C_{1-6}$-alkoxy with mono-, di-, or trimethoxy substituted benzylamine to form a compound of formula XIII

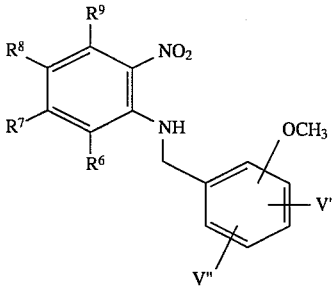  (XIII)

wherein $R^6$, $R^7$, $R^8$ and $R^9$ have the meanings defined above, and V' and V" independently are hydrogen or methoxy, and reacting the compound with ethyloxalylchloride to form a compound of formula XIV

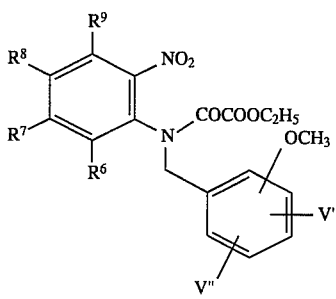  (XIV)

wherein $R^6$, $R^7$, $R^8$ and $R^9$ have the meanings defined above, and V' and V" independently are hydrogen or methoxy, and then either hydrogenation to form the intermediate cyclized N-hydroxy compound followed by deoxygenation or cyclization by hydrogenation to form a compound of formula XV

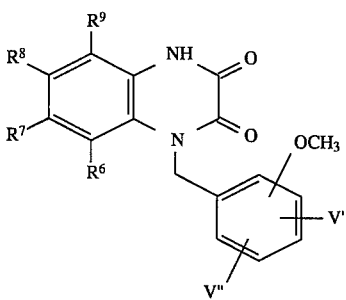  (XV)

wherein $R^6$, $R^7$, $R^8$ and $R^9$ have the meanings defined above, and V' and V" independently are hydrogen or methoxy, halogenating the compound of formula XV, reacting the resulting compound with hydrazine followed by acylating with an acylchloride of the general formula VI as defined above, and then cyclization to form a compound of formula XVI

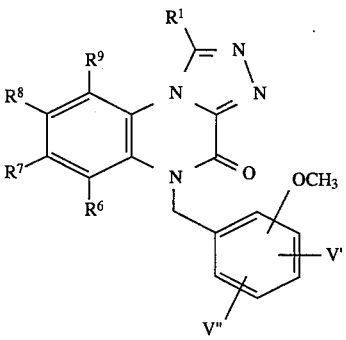  (XVI)

wherein $R^6$, $R^7$, $R^8$ and $R^9$ have the meanings defined above, and V' and V" independently are hydrogen or methoxy, and hydrolysis to form a compound of formula I, wherein X' and X" are $C_{1-6}$-alkoxy, or d) hydrolysing a compound of formula I, wherein X' and X" are $C_{1-6}$-alkoxy with aqueous base to form a compound of formula I, wherein X' is hydroxy, and X" is $C_{1-6}$-alkoxy, or e) reacting a compound of formula I, wherein X' is hydroxy or $C_{1-6}$-alkoxy, and X" is $C_{1-6}$-alkoxy with halotrimethylsilane to form a compound of formula I, wherein X' and X" are hydroxy.

The pharmacological properties of the compounds of the present invention can be illustrated by determining their capability for displacing radioactively labelled 2-amino-3-hydroxy-5-methyl-4-isoxazolepropionic acid (AMPA) from the AMPA type receptors. The antagonistic properties of the compounds is demonstrated by their capability to antagonize quisqualic acid stimulated spreading depression in chicken retina.

The displacement activity of the compounds may be shown by determining the $IC_{50}$ value which represents the concentration (μM) which causes a displacement of 50% of the specific binding of $^3$H-AMPA.

The antagonism is measured by determining the $IC_{50}$ value which represents the concentration which produces a 50% maximal inhibition of quisqualic acid stimulated spreading depression in chicken retina.

$^3$H-AMPA Binding (Test 1)

500 μl of thawed rat cerebral cortical membrane homogenate in Tris-HCl (30 mM), $CaCl_2$ (2.5 mM) and KSCN (100 mM) pH 7.1 were incubated at 0° C. for 30 min. with 25 μl $^3$H-AMPA (5 nM final concentration) and the test compound and buffer. Nonspecific binding was determined by incubation with L-glutamic acid (600 μM final concentration). The binding reaction was terminated by adding 5 ml of ice-cold buffer followed by filtration through Whatman GF/C glass fibre filters and 2×5 ml wash with ice-cold buffer. Bound radioactivity was measured by scintillation counting. $IC_{50}$ was determined by Hill analysis of at least four concentrations of test compound.

Spreading Depression (Test 2)

Chicks (3–10 days old) were decapitated, the eyes enucleated and sectioned along the equatorial plane. After removal of the anterior chamber and the vitreous body, the posterior chamber of each eye was placed in a small petri dish containing a physiological saline solution (P.S.S.) of the following composition (mM) NaCl (100), KCl (6.0), $CaCl_2$ (1.0), $MgSO_4$ (1.0), $NaHCO_3$ (30), $NaH_2PO_4$ (1.0), glucose (20).

The solution was saturated with 100% $O_2$ and maintained at a temperature of 26° C.

The eyes were initially incubated in normal P.S.S. for 15–30 min. and then transferred to P.S.S. containing quisqualate (1 μg/ml). In this "stimulating solution" S.D.s start spontaneously usually from the edge of the retina, and can be easily observed by eye. The time taken for an S.D. to start in each eye was measured.

After a further 15 min. of incubation in normal P.S.S. the eyes were transferred to normal P.S.S. containing the test compound and incubated for 15 min. Thereafter the eyes were transferred to a "stimulating solution" containing the same concentration of the test compound. The time taken for an S.D. to start in each eye was measured again. The eyes were then placed back in normal P.S.S. and after 15 min. the time taken for S.D. to start was measured again, in order to assess the degree of recovery from any drug effects.

An increase in the time taken for S.D. to start of 30 seconds more than the control time is considered 100% inhibition of S.D. The drug effects therefore are expressed as the percentage maximum response obtained for a given dose. The test value can be quoted therefore as the concentration (μM) of test substance which produces a 50% maximal inhibition ($IC_{50}$).

Test results obtained by testing some compounds of the present invention are shown in the following table 1.

TABLE 1

| Compound of example | TEST 1 $IC_{50}$ μM | TEST 2 $IC_{50}$ μM |
| --- | --- | --- |
| 20 | 0.26 | 0.4 |
| 30 | 0.48 | 1.4 |

The pharmaceutical preparations of compositions comprising the compounds of the invention may be administered to humans or animals by oral, rectal or parenteral route.

An effective amount of the active compound or a pharmaceutically acceptable salt thereof may be determined in accordance with the usual factors, such as the nature and severity of the condition and the weight of the mammal requiring treatment.

Conventional excipients are such pharmaceutically acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or colouring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 10–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet which may be prepared by conventional tabletting techniques contains:

| Core: | |
| --- | --- |
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | 1 mg |

| Coating: | | |
|---|---|---|
| HPMC | approx. | 9 mg |
| *Mywacett ® 9-40T | approx. | 0.9 mg |

*Acylated monoglyceride used as plasticizer for film-coating

The free compounds of the present invention which form alkali metal or alkaline earth metal salts may be employed in such salt form. Such alkali metal or earth alkali metal salts are ordinarily formed by reacting the compound with an equivalent amount or excess of the selected alkali metal or earth alkali metal as the hydroxide, frequently and suitably by admixture in the presence of a neutral solvent, from which the salt may be precipitated or recovered in other conventional manner, e.g. by evaporation. Administration of a compound of the invention is often preferably in the form of a pharmaceutically acceptable water-soluble alkali metal or earth alkali metal salt thereof, and orally, rectally, or parenterally in the form of a pharmaceutical composition wherein it is present together with a pharmaceutically acceptable liquid or solid carrier or diluent.

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective AMPA antagonistic amount of the active ingredient commensurate with the intended daily dosage range to be employed. Tablets containing 10 mg to 200 mg of active ingredient or, more specified 50 mg, per tablet, are accordingly suitable representative unit dosage forms.

Due to their high degree of AMPA antagonistic activity and their low toxicity, together presenting a most favourable therapeutic index, the compounds of the invention may be administered to a subject, e.g. a living animal body, in need of such treatment, elimination, alleviation, or amelioration of an indication which is sensitive to a change in the AMPA receptor condition, e.g. sclerosis, Parkinsonism, Alzheimer's disease, Huntington's disease, epilepsy, deficiencies seen after ischemia, anoxia, hypoglycemia, head and spinal cord trauma, psychosis, muscle rigidity, emesis and analgesia, often preferably in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Suitable dosage ranges are 10–200 milligrams daily, preferably 50–100 milligrams daily, and especially 70–100 milligrams daily, depending as usual upon the exact mode of administration, form in which administered, the indication towards which the administration is directed, the subject involved and the body weight of the subject involved, and the preference and experience of the physician or veterinarian in charge.

Such method of treating may be described as the treatment of an indication caused by or related to hyperactivity of the excitatory neurotransmitters, and particularly the AMPA receptors in a subject in need thereof, which comprises the step of administering to the said subject a neurologically effective amount of an AMPA antagonistic compound of the invention, or a pharmaceutically acceptable salt thereof.

Furthermore, the present invention relates to the use of a compound of the invention for preparing a medicament for treating an indication caused by or related to hyperactivity of the excitatory neurotransmitters, and particularly the AMPA receptors in a subject in need thereof.

The invention will now be described in further detail with reference to the following examples:

EXAMPLE 1

A. 3-Chloro-2-(2-ethoxalylhydrazino)-6-nitroquinoxaline

To a stirred suspension of 2.1 g (~8.8 mmol) of 3-chloro-2-hydrazino-6-nitroquinoxaline in 125 ml of dry tetrahydrofuran was added 1.35 ml (~9.8 mmol) of dry triethylamine and then gradually 1.1 ml (~9.9 mmol) of ethyl oxalylchloride. Stirring was continued at 25° C. for 90 min. The evaporated reaction mixture was stirred with water to give 2.9 g (~96%) of the title compound.

$^1$H-NMR (DMSO-$d_6$): δ 11.4 (1H, s), 10.4 (1H, br. s), 8.7 (1H, d, J=3.5 Hz), 8.4 (1H, dd, J=3.5 Hz and 9.2 Hz), 7.8 (1H, d, J=9.2 Hz).

B. 4-Chloro-1-ethoxycarbonyl-7-nitro[1,2,4]triazolo[4,3-a]quinoxaline

A mixture of 2.0 g (~5.9 mmol) of 3-chloro-2-(2-ethoxalylhydrazino)-6-nitroquinoxaline and 20 ml of phosphorus oxychloride was refluxed for 90 min. After cooling to 50° C. the reaction mixture was poured into ice-water to give 1.7 g (~90%) of the title compound as a precipitate.

C. 1-Ethoxycarbonyl-7-nitro[1,2,4]triazolo[4,3-a]quinoxalin-4(5H)-one

A mixture of 1.5 g (~4.7 mmol) of 4-chloro-1-ethoxycarbonyl-7-nitro[1,2,4]triazolo[4,3-a]quinoxaline and 25 ml of glacial acetic acid was refluxed for 60 min. After cooling to 25° C. the precipitate was filtered off to give 1.5 g of a crude product. Purification by column chromatography (silica gel; eluent: ethyl acetate) gave 1.2 g (~90%) of the title compound.

$^1$H-NMR (DMSO-$d_6$): δ 8.5 (1H, d, J=9.2 Hz), 8.08 (1H, d, J=3.5 Hz), 7.8 (1H, dd, J=3.5 Hz and 9.2 Hz), 4.55 (2H, q), 1.4 (3H, t).

The following example was prepared in an analogous manner from 3-chloro-2-hydrazino-6-nitroquinoxaline and ethyl succinylchloride.

EXAMPLE 2

1-(2-Ethoxycarbonylethyl)-7-nitro[1,2,4]triazolo[4,3-a]quinoxalin-4(5H)-one

M.p. 220° C. decomp.

$^1$H-NMR (DMSO-$d_6$): δ 12.4 (1H, s), 8.27 (1H, d, J=9.2 Hz), 8.2 (1H, d, J=3.5 Hz), 8.1 (1H, dd, J=3.5 Hz and 9.2 Hz), 4.1 (2H, q), 3.6 (2H, t), 3.05 (2H, t), 1.2 (3H, t).

EXAMPLE 3

1-(2-Carboxyethyl)-7-nitro[1,2,4]triazolo[4,3-a]quinoxalin-4(5H)-one 0.5 g (~1.5 mmol) of 1-(2-ethoxycarbonylethyl)-7-nitro[1,2,4]triazolo[4,3-a]quinoxalin-4(5H)-one was added to a mixture of 50 ml of water and 1.5 ml of 2N sodium hydroxide. Stirring was continued for 24 h at 25° C. Addition of 4N hydrochloric acid to pH=2–3 gave the title compound (0.42 g; 92%) as a precipitate. M.p.>300° C. decomp.

$^1$H-NMR (DMSO-$d_6$): δ 12.4 (1H, s), 12.35 (1H, s), 8.25 (1H, d, J=9.2 Hz), 8.2 (1H, d, J=3.5 Hz), 8.12 (1H, dd, J=3.5 Hz and 9.2 Hz), 3.6 (2H, t), 3.0 (2H, t).

EXAMPLE 4

A. 1-Benzyloxy-7-cyano-6-trifluoromethylquinoxaline-2,3(1H,4H)-dione

To a solution of 10.0 g (~36.9 mmol) of 7-cyano-1-hydroxy-6-trifluoromethylquinoxaline-2,3 (1H,4H)-dione in a mixture of 700 ml of ethanol and 175 ml of 1M potassium dihydrogen phosphate buffer pH 7.4 was added 14 g (~81 mmol) of benzylbromide. Stirring was continued for 2 h at 25° C. The precipitate was filtered off and washed with ice-cold ethanol to give the title compound (9.9 g; 75%).

$^1$H-NMR (DMSO-$d_6$): δ 7.75 (1H, s), 7.65 (2H, m), 7.5 (1H, s), 7.4 (3H, m), 5.2 (2H, s).

B. 1-Benzyloxy-3-chloro-7-cyano-6-trifluoromethylquinoxalin-2(1H)-one

To a solution of 7.0 g (~19.4 mmol) of 1-benzyloxy-7-cyano-6-trifluoromethylquinoxaline-2,3 (1H,4H)-dione in 250 ml of dry N,N-dimethylformamide was added at 0° C. 38.5 ml of 1.93M phosgene in toluene (~74.3 mmol). Stirring was continued at 24° C. for 20 h. The evaporated reaction mixture was stirred with water to give the title compound (6.6 g; 89%).

$^1$H-NMR (DMSO-$d_6$): δ 8.45 (1H, s), 8.3 (1H, s), 7.7 (2H, m), 7.45 (3H, m), 5.3 (2H, s).

C. 1-Benzyloxy-7-cyano-3-hydrazino-6-trifluoromethylquinoxalin-2(1H)-one

To a solution of 5.2 g (13.7 mmol) of 1-benzyloxy-3-chloro-7-cyano-6-trifluoromethylquinoxalin-2 (1H)-one in 150 ml of dichloromethane was added 2.7 ml of hydrazine monohydrate (~55.7 mmol) at 0° C. Stirring was continued at 0° C. for 1 h. The evaporated reaction mixture was stirred with water to give the title compound (5.0 g; 97%).

$^1$H-NMR (DMSO-$d_6$): δ 7.8 (1H, s), 7.7 (1H, s), 7.6 (2H, m), 7.4 (3 H, m), 5.25 (2H, s).

D. 1-Benzyloxy-7-cyano-3-(2-ethoxysuccinylhydrazino)-6-trifluoromethylquinoxalin-2(1H)-one To a suspension of 2.1 g (~5.6 mmol) of 1-benzyloxy-7-cyano-3-hydrazino-6-trifluoromethylquinoxalin-2(1H)-one in 100 ml of dry tetrahydrofuran was added 0.85 ml (~6.18 mmol) of dry triethylamine followed by the addition of 0.88 ml (~6.18 mmol) of ethyl succinylchloride. Stirring was continued at 24° C. for 90 min. The evaporated reaction mixture was stirred with water to give the title compound (2.8 g; 98%).

$^1$H-NMR (DMSO-$d_6$): δ 10.4 (1H, br. s), 10.2 (1H, s), 8.05 (1H, s), 7.8 (1H, s), 7.75 (2H, m), 7.45 (3H, m), 5.35 (2H, s), 4.1 (2H, q), 2.6 (2H, s), 1.2 (3H, t).

E. 7-Cyano-3-(2-ethoxysuccinylhydrazino)-1-hydroxy-6-trifluoromethylquinoxalin-2(1H)-one A solution of 2.7 g (~5.4 mmol) of 1-benzyloxy-7-cyano-3-(2-ethoxysuccinylhydrazino)-6-trifluoromethylquinoxalin-2(1H)-one in a mixture of 150 ml of ethyl acetate and 150 ml of ethanol was hydrogenated at atm. pressure by using 5% Pd—C (0.2 g) as a catalyst. The reaction mixture was filtered and the filtrate was evaporated in vacuo to give the title compound (2.2 g; 92%).

$^1$H-NMR (DMSO-$d_6$): δ 12.5 (1H, br. s), 10.3 (1H, br. s), 10.2 (1H, s), 8.15 (1H, s), 7.8 (1H, s), 4.05 (2H, q), 2.5 (2H, s), 1.15 (3H, t).

F. 7-Carbamoyl-1-(2-carboxyethyl)-8-trifluoromethyl[1,2,4]triazolo[4,3-a]quinoxalin-4 (5H)-one To a solution of 0.2 g (~0.48 mmol) of 7-cyano-3-(2-ethoxysuccinylhydrazino)-1 -hydroxy-6-trifluoromethylquinoxalin-2(1H)-one in 8 ml of dry N,N-dimethylformamide was added 0.18 g (~0.69 mmol) of triphenylphosphine. Stirring was continued at 120° C. for 48 h. The evaporated reaction mixture was stirred with 10 ml of 2N sodium hydroxide for 72 h. To the filtered reaction mixture was added 4N hydrochloric acid to pH=2. The precipitate was filtered off to give 70 mg (~40%) of the title compound.

$^1$H-NMR (DMSO-$d_6$): δ 12.5 (2H, br. s), 8.2 (2H, s), 7.8 (1H, s), 7.5 (1H, s).

EXAMPLE 5

A. 5-Benzyloxy-7-cyano-1-(2-ethoxycarbonylethyl)-8-trifluoromethyl[1,2,4]triazolo[4,3-a]quinoxalin-4(5H)-one A mixture of 5.3 g (~10.5 mmol) of 1-benzyloxy-7-cyano-3-(2-ethoxysuccinylhydrazino)-6-trifluoromethylquinoxalin-2(1H)-one and 50 ml of phosphorus oxychloride was stirred at 70° C. for 90 min. The mixture was poured into 300 ml of ice-water to give a crude product as a precipitate. Column chromatography (silica gel; eluent=ethyl acetate) gave the title compound (1.06 g ~21%).

$^1$H-NMR (DMSO-$d_6$): δ 8.40 (1H), s), 8.28 (1H, s), 7.7 (2H, m), 7.95 (3H, m), 5.33 (2H, s), 4.13 (2H, q), 3.75 (2H, t), 3.05 (2H, t), 1.2 (3H, t). MS (m/e): 485 (M$^+$, 10%).

B. 7-Cyano-1-(2-ethoxycarbonylethyl)-8-trifluoromethyl[1,2,4]triazolo[4,3-a]quinoxalin-4(5H)-one A solution of 1.0 g (~2.1 mmol) 5-benzyloxy-7-cyano-1-(2-ethoxycarbonylethyl)-8 -trifluoromethyl[1,2,4]triazolo[4,3-a]quinoxalin-4(5H)-one in a mixture of 50 ml of ethanol and 50 ml of ethyl acetate was hydrogenated at atmospheric pressure by using 5% Pd—C (0.2 g) as a catalyst. Filtration followed by evaporation in vacuo gave the N-hydroxy derivative as yellow crystals.

The crude intermediate was dissolved in 30 ml of dry N,N-dimethylformamide and 1.5 g (5.8 mmol) of triphenylphosphine was added. The reaction mixture was stirred at 120° C. for 20 h. Evaporation in vacuo followed by flash

C. 1-(2-Carboxyethyl)-7-cyano-8-trifluoromethyl [1,2,4]triazolo[4,3-a]quinoxalin-4 (5H)-one A mixture of 0.5 g (~1.3 mmol) of 7-cyano-1-(2-ethoxycarbonylethyl)-8-trifluoromethyl[1,2,4]triazolo[4,3-a]quinoxalin-4(5H)-one and 25 ml of 1N sodium hydroxide was stirred at 25° C. for 2 h. The solution was cooled in an ice bath and acidified with 4N hydrochloric acid to pH=2. The precipitate was filtered off to give 0.29 g (~63%) of the title compound.

$^1$H-NMR (DMSO-$d_6$): δ 12.6 (1H, s), 12.3 (1H, s), 8.35 (1H, s), 7.95 (1H, s), 3.65 (2H, t), 2.95 (2H, t).

EXAMPLE 6

A. 3-Chloro-2-(2-ethoxysuccinylhydrazino)-6-trifluoromethylquinoxaline

Ethyl succinylchloride (0.60 ml, 4.21 mmol) was added dropwise to a stirred solution of 3-chloro-2-hydrazino-6-trifluoromethylquinoxaline (1.1 g, 4.17 mmol) and dry triethylamine (0.60 ml, 4.30 mmol) in 5 ml of dry tetrahydrofuran. The mixture was stirred at room temperature for 2 h, and filtered. The filtrate was evaporated to dryness and the residue was triturated with water to give 1.60 g (98%) of crude title compound.

B. 1-(2-Ethoxycarbonylethyl)-7-trifluoromethyl [1,2,4]triazolo[4,3-a]quinoxalin-4(5H)-one A solution of crude 3-chloro-2-(2-ethoxysuccinylhydrazino)-6-trifluoromethylquinoxaline (1.41 g, 3.6 mmol) in 7 ml of phosphorus oxychloride was refluxed at 120° C. for 1 h, cooled and poured into 150 ml of ice/water. The mixture was stirred at 0° C. for 3 h and then filtered to give 0.94 g (70%) of the intermediate 4-chlorotriazoloquinoxaline. Then it was refluxed in 10 ml of glacial acetic acid for 2 h, evaporated to dryness and the residue was triturated with water. Recrystallization from ethanol yielded 240 mg (19%) of the title compound. M.p. 262° C. (DSC).

$^1$H-NMR (DMSO-$d_6$): δ 1.21 (t, 3H), 3.05 (t, 2H), 3.61 (t, 2H), 4.11 (q, 2H), 7.62–7.71 (m, 2H), 8.24 (d, 1H), 12.26 (br. s, 1H); MS (m/e): 354 (M$^+$, 8%).

EXAMPLE 7

1-(2-Carboxyethyl)-7-trifluoromethyl[1,2,4]triazolo [4,3-a]quinoxalin-4(5H)-one A suspension of 1-(2-ethoxycarbonylethyl)-7-trifluoromethyl[1,2,4]triazolo[4,3-a]quinoxalin-4(5H)-one (177 mg, 0.5 mmol) in 6 ml of 1N sodium hydroxide was stirred at room temperature for 150 min. The solution was cooled in an ice bath and acidified with 4M hydrochloric acid to pH 1. The precipitate was isolated by filtration, washed with water, ethanol and ether to give 131 mg (80%) of the title compound. M.p. 333° C. (DSC).

$^1$H-NMR (DMSO-$d_6$): δ 2.99 (t, 2H), 3.58 (t, 2H), 7.61–7.72 (m, 2H), 8.25 (d, 1H), 12.3 (br. s, 2H); MS (m/e): 326 (M$^+$, 14%).

EXAMPLE 8

A. 1-Benzyloxy-7-trifluoromethylquinoxaline-2,3(1H, 4H)-dione

Benzyl bromide (72 ml, 0.60 mol) was added to a suspension of 1-hydroxy-7-trifluoromethylquinoxaline-2,3(1H,4H)-dione (49.2 g, 0.20 mol) in 2.5 l of ethanol and 800 ml of 1M potassium dihydrogen phosphate buffer (pH 7.4). The mixture was stirred at room temperature overnight, and filtered. The precipitate was washed with water and dried to give 59.5 g (89%) of the title compound. M.p.>220° C. decomp.

$^1$H-NMR (DMSO-$d_6$): δ 5.23 (s, 2H), 7.29–7.61 (m, 8H), 12.4 (br. s, 1H).

B. 1-Benzyloxy-3-chloro-7-trifluoromethylquinoxalin-2(1H)-one

A solution of 20% phosgene in toluene (120 ml, 0.23 mol) was added to a solution of 1-benzyl-7-trifluoromethylquinoxaline-2,3(1H,4H)-dione (27 g, 80 mmol) in 300 ml of dry N,N-dimethylformamide with stirring at 0° C. The mixture was stirred at room temperature overnight and evaporated to dryness. The residue was triturated with ice/water, filtered and dried in vacuo over phosphorus pentoxide to give 27.4 g (96%) of the title compound. M.p. 148°–150° C.

$^1$H-NMR (DMSO-$d_6$): δ 5.33 (s, 2H), 7.38–7.44 (m, 3H), 7.56–7.62 (m, 3H), 7.72 (dd, 1H), 8.02 (d, 1H).

C. 1-Benzyloxy-3-hydrazino-7-trifluoromethylquinoxalin-2(1H)-one

A mixture of 1-benzyloxy-3-chloro-7-trifluoromethylquinoxalin-2(1H)-one (27 g, 76 mmol) and hydrazine hydrate (14.7 ml, 0.30 mol) in 250 ml of dichloromethane was stirred at 0° C. for 2 h. The precipitate was isolated by filtration, washed with dichloromethane and water and dried to give 22.8 g (76%) of the title compound. M.p. 174°–176° C.

$^1$H-NMR (DMSO-$d_6$): δ 5.29 (s, 2H), 7.35–7.61 (m, 8H).

D. 1-Benzyloxy-3-[2-[(diethoxyphosphoryl) acetyl]hydrazino]-7-trifluoromethylquinoxalin-2(1H)-one A solution of (diethoxyphosphoryl)acetyl chloride (5.8 g, 27 mmol) in 40 ml of dry tetrahydrofuran was added to a solution of 1-benzyloxy-3-hydrazino-7-trifluoromethylquinoxalin-2(1H)-one (8.75 g, 25 mmol) and dry triethylamine (3.6 ml, 27 mmol) in 200 ml of dry tetrahydrofuran. The mixture was stirred at room temperature for 3 h and filtered. The filtrate was evaporated to dryness, and the residue was crystallized by trituration with water (200 ml) to give 12.85 g (97%) of the title compound. M.p. 163°–166° C.

$^1$H-NMR (DMSO-$d_6$): δ 1.27 (t, 6H), 3.07 (d, 2H), 4.10 (quint, 4H), 5.35 (s, 2H), 7.36–7.61 (m, 8H), 10.10 and 10.27 (br. s, 2H).

E. 3-[2-[(Diethoxyphosphoryl)acetyl]hydrazino]-1-hydroxy-7-trifluoromethylquinoxalin-2(1H)-one A solution of 1-benzyloxy-3-[2-[(diethoxyphosphoryl)acetyl]hydrazino]-7-trifluoromethylquinoxalin-2(1H)-one (5.28 g, 10 mmol) in 500 ml of ethanol was hydrogenated at atmospheric pressure and room temperature for 1 h in the presence of 250 mg of 5% palladium on carbon. The catalyst was removed by filtration, and the filtrate was evaporated to dryness. The residue was triturated with ether and light petroleum to give 4.0 g (91%) of the title compound. M.p. 193°–196° C.

$^1$H-NMR (DMSO-d$_6$): δ 1.26 (t, 6H), 3.05 (d, 2H), 4.08 (quint, 4H), 7.54 (s, 2H), 7.78 (s, 1H), 9.96 (br. s, 1H), 10.26 (br. s, 1H), ca. 12.35 (br. s, 1H).

F.
1-[(Diethoxyphosphoryl)methyl]-7-trifluoromethyl [1,2,4]triazolo[4,3-a]quinoxalin-4(5 H)-one A solution of 3-[2-[(diethoxyphosphoryl)acetyl]hydrazino]-1-hydroxy-7-trifluoromethylquinoxalin-2(1H)-one (438 mg, 1 mmol) and triphenylphosphine (525 mg, 2 mmol) in 25 ml of glacial acetic acid was heated under reflux overnight (ca. 15 h). The mixture was evaporated to dryness, and the residue was flash chromatographed (SiO$_2$) with dichloromethane to remove excess triphenylphosphine, then with ethyl acetate to remove triphenylphosphine oxide, and finally with 5% acetic acid in ethyl acetate to give 161 mg (40%) of the title compound. M.p. 224°–226° C., dec. (ethanol).

$^1$H-NMR (DMSO-d$_6$): δ 1.17 (t, 6H), 4.05 (quint, 4H), 4.27 (d, 2H), 7.54 (dd, 1H), 7.65 (d, 1H), 8.33 (d, 1H); MS (m/e): 404 (M$^+$, 13%).

(C$_{15}$H$_{16}$F$_3$N$_4$O$_4$P.0.25 H$_2$O) Calc.: C 44.07 H 4.07 N 13.71 Found: C 44.05 H 4.11 N 13.69

The compounds of the following examples were prepared in an analogous manner from the appropriate 1-hydroxyquinoxaline-2,3(1H,4H)-diones and (diethoxyphosphoryl) acid chlorides prepared by conventional procedures.

EXAMPLE 9

1-[2-(Diethoxyphosphoryl)ethyl]-7-trifluoromethyl [1,2,4]triazolo[4,3-a]quinoxalin-4(5H)-one M.p. 242°–248° C. dec.

$^1$H-NMR (DMSO-d$_6$): δ 1.27 (t, 6H), 2.34–2.54 (m, 2H), 3.48–3.65 (m, 2H), 4.07 (quint, 4H), 7.61–7.72 (m, 2H), 8.10 (d, 1H).

EXAMPLE 10

7-Cyano-1-[(diethoxyphosphoryl)methyl]-8-trifluoromethyl[1,2,4]triazolo[4,3-a]quinoxalin-4(5H)-one M.p. 200°–203° C.

$^1$H-NMR (DMSO-d$_6$): δ 1.19 (t, 6H), 4.07 (quint, 4H), 4.41 (d, 2H), 7.91 (s, 1H), 8.63 (s, 1H); IR (KBr): 2238, 1714 cm$^{-1}$.

EXAMPLE 11

1-[1-(Diethoxyphosphoryl)ethyl]-7-trifluoromethyl [1,2,4]triazolo[4,3-a]quinoxalin-4 (5H)-one M.p. 238°–241° C.; $^1$H-NMR(DMSO-d$_6$): δ 1.08 (t, 3H), 1.14 (t, 3H), 1.75 (dd, 3H), 3.95 (quint, 2H), 4.04 (quint, 2H), 4.60 (dq, 1H), 7.60 (dd, 1H), 7.69 (dd, 1H), 8.40 (dd, 1H).

EXAMPLE 12

1-[1-(Diethoxyphosphoryl)propyl]-7-trifluoromethyl[1,2,4]triazolo[4,3-a]quinoxalin-4 (5H)-one M.p.>130° C. decomp; $^1$H-NMR (DMSO-d$_6$): δ 0.97 (t, 3H), 1.06 (t, 3H), 1.13 (t, 3H), 2.12–2.56 (m, 2H), 3.92 (quint, 2H), 4.03 (quint, 2H), 4.34–4.54 (m, 1H), 7.66 (dd, 1H), 7.71 (d, 1H), 8.49 (d, 1H), 12.3 (br s, 1H).

EXAMPLE 13

A. 3-Chloro-6-cyano-2-[2-[(diethoxyphosphoryl) acetyl]hydrazino]quinoxaline

A solution of (diethoxyphosphoryl)acetyl chloride (2.15 g, 10 mmol) in 20 ml of dry tetrahydrofuran was added to a solution of 3-chloro-6-cyano-2-hydrazinoquinoxaline (2.0 g, 9 mmol) and dry triethylamine (1.4 ml, 10 mmol) in 100 ml of dry tetrahydrofuran. The mixture was stirred at room temperature overnight, and filtered. The filtrate was evaporated, and the title compound was isolated as a semisolid residue, which was used in the next step without further purification; $^1$H-NMR (DMSO-d$_6$): δ 1.26 (t, 6H), 3.09 (d, 2H), 4.10 (quint, 4H), 7.71 (d, 1H), 7.97 (dd, 1H), 8.39 (d, 1H).

B. 7-Cyano-1-[(diethoxyposphoryl)methyl][1,2,4] triazolo[4,3-a]quinoxalin-4(5H)-one A solution of crude 3-chloro-6-cyano-2-[2-[(diethoxyphosphoryl)acetyl]hydrazino]quinoxaline] in 100 ml of glacial acetic acid was heated under reflux for 1 h under nitrogen. The mixture was evaporated, and the residue was triturated with water and recrystallized from acetonitrile to give 1.87 g (57% overall) of the title compound, m.p. 223°–225° C.; $^1$H-NMR (DMSO-d$_6$): δ 1.17 (t, 6H), 4.07 (quint, 4H), 4.29 (d, 2H), 7.72 (d, 1H), 7.80 (dd, 1H), 8.37 (d, 1H), 12.32 (s, 1H).

EXAMPLE 14

8-Chloro-1-[(diethoxyphosphoryl)methyl][1,2,4] triazolo[4,3-a]quinoxalin-4(5H)-one The title compound was prepared from 2,6-dichloro-3-hydrazinoquinoxaline (830 mg, 3.62 mmol) and (diethoxyphosphoryl)acetyl chloride (800 mg, 3.72 mmol) by the method described in example 13 (619 mg; 44%). M.p. 223°–227° C. (ethanol); $^1$H-NMR (DMSO-d$_6$): δ 1.19 (t, 6H), 4.07 (quint: 4H), 4.32 (d, 2H), 7.39 (d, 1H), 7.56 (dd, 1H), 8.19 (d, 1H), 12.2 (s, 1H).

EXAMPLE 15

1-[(Diethoxyphosphoryl)methyl]-7-nitro[1,2,4] triazolo[4,3-a]quinoxalin-4(5H)-one The title compound was prepared from 3-chloro-2-hydrazino-6-nitroquinoxaline and (diethoxyphosphoryl)acetyl chloride by the method described in example 13. The crude product was hydrolyzed without further purification (example 28).

EXAMPLE 16

1-[(Diethoxyphosphoryl)methyl]-8-nitro-7-trifluoromethyl[1,2,4]triazolo[4,3-a]quinoxalin-4(5H)-one Powdered potassium nitrate (1.82 g, 18 mmol) was added to a stirred solution of 1-[(diethoxyphosphoryl)methyl]-7-trifluoromethyl[1,2,4]triazolo [4,3-a]quinoxalin-4(5H)-one (3.7 g, 9.15 mmol) in 50 ml of conc. sulfuric acid at 0° C. The mixture was stirred at room temperature overnight, and quenched in ice/water (300 g). The aqueous phase was extracted with ethyl acetate (5×100 ml), and the combined organic extracts were dried with anhydrous sodium sulfate, and evaporated. The residue was triturated with ether to give 3.25 g (79%) of the title compound, m.p. 222°–228° C.; $^1$H-NMR (DMSO-$d_6$): δ 1.20 (t, 6H), 4.10 (quint, 4H), 4.39 (d, 2H), 7.88 (s, 1H), 8.96 (s, 1H), 12.67 (br s, 1H).

EXAMPLE 17

8-Amino-1[(diethoxyphosphoryl)methyl]-7-trifluoromethyl[1,2,4]triazolo[4,3-a]quinoxalin-4(5H)-one A solution of 1-[(diethoxyphosphoryl)methyl]-8-nitro-7-trifluoromethyl[1,2,4]triazolo[4,3-a]quinoxalin-4(5H)-one (3.25 g, 7.2 mmol) in 500 ml of ethanol was hydrogenated at 40 psi and room temperature for 6 h in the presence of Raney-Ni. The catalyst and precipitated solid was isolated by filtration and washed with ethanol. The ethanolic filtrate was discharged, and the filter-cake was washed with N,N-dimethylformamide. The filtrate was evaporated, and the residue was triturated with water to give the title compound as a light yellow solid (2.4 g, 80%), m.p. 260°–263° C.; $^1$H-NMR (DMSO-$d_6$): δ 1.18 (t, 6H), 4.07 (quint, 4H), 4.13 (d, 2H), 5.74 (br s, 2H), 7.42 (s, 1H), 7.69 (s, 1H), 11.8 (s, 1H).

EXAMPLE 18

A. 4-Bromo-1-(2,4-dimethoxybenzylamino)-2-nitronaphthalene

To a solution of 4-bromo-1-methoxy-2-nitronaphthalene (3,5 g, 12.5 mmol) in dry tetrahydrofuran (15 ml) was dropwise added 2,4-dimethoxybenzylamine (8,5 g, 41,6 mmol) in dry tetrahydrofuran (15 ml). The mixture was stirred at room temperature overnight and evaporated to dryness. The residue was submitted to flash chromatography (SiO$_2$) eluting with toluene/ethyl acetate (1:1). The product was taken up in ethyl acetate and precipitated with light petroleum to give 4.1 g (78%) of the title compound. M.p. 104°–105° C.

$^1$H-NMR (CDCl$_3$): δ 3.72 (s, 3H), 3.80 (s, 3H), 4.70 (d, 2H), 6.40 (m, 2H), 7.08 (d, 1H), 7.58 (m, 1H), 7.75 (m, 1H), 8.20 (d, 1H), 8.38 (m, 2H), 8.75 (m, 1H).

B. 4-Bromo-2-nitro-1-(N-(2,4-dimethoxybenzyl))ethoxalylaminonaphthalene

To a solution of 4-bromo-1-(2,4-dimethoxybenzylamino)-2-nitronaphthalene (4.1 g, 9.7 mmol) and triethylamine (2.7 ml, 19,5 mmol) in tetrahydrofuran (70 ml) was dropwise added ethyl oxalyl chloride (2,2 ml, 19,5 mmol) in tetrahydrofuran (15 ml). The mixture was stirred at room temperature overnight, and filtered. The filtrate was evaporated to dryness and the residue submitted to flash chromatography (SiO$_2$), eluting with toluene graduated to toluene/ethyl acetate (1:1) to give 3.97 g (79%) of the title compound. M.p. 108°–109° C. $^1$H-NMR (CDCl$_3$): δ 1.02 (t, 3H), 3.02 (s, 3H), 3.75 (s, 3H), 3.98 (q, 2H), 4.85 (d, 1H), 5.20 (d, 1H), 6.05 (d, 1H), 6,38 (m, 1H), 7.22 (m, 1H), 7.65 (m, 1H), 7.78 (m, 1H), 7.95 (m, 1H), 8.20 (s, 1H), 8.30 (m, 1H).

C. 1-(2,4-dimethoxybenzyl)benzo[f]quinoxaline-2,3(1H, 4H)-dione

A solution of 4-bromo-2-nitro-1-(N-(2,4-dimethoxybenzyl))ethoxalylaminonaphthalene (3.97 g, 7.7 mmol) in N,N-dimethylformamide (350 ml) and ethanol (450 ml) was hydrogenerated at atmospheric pressure and room temperature in the presence of Raney-Ni (1 g). The catalyst was removed by filtration and the filtrate evaporated to dryness. The residue was taken up in ethanol (200 ml), glacial acetic acid (10 ml) was added and the mixture was stirred at 80° C. for 10 h. The mixture was concentrated in vacuo to 30 ml and allowed to precipitate. The product was isolated by filtration to 3.75 (s, 3H), 3.80 (s, 3H), 5.22 (bs, 2H), 6.45 (m, 1H), 6.65 (m, 1H), 7.30 (m, 4H), 7.75 (d, 1H), 7,90 (m, 2H).

D. 3-Chloro-1-(2,4-dimethoxybenzyl)benzo[f]quinoxalin-2(1H)-one

A solution of 20% phosgene in toluene (10 ml, 19 mmol) was added to a solution of 1-(2,4-dimethoxybenzyl)benzo[f]quinoxaline-2,3(1H, 4H)-dione (950 mg; 2.6 mmol) in dry N,N-dimethylformamide (100 ml) with stirring at 0° C. The mixture was stirred at room temperature overnight, and evaporated to dryness. The residue was triturated with ice/water, filtered and dried in vacuo to give 900 mg (90%) of the title compound, m.p. 186° C. $^1$H-NMR (DMSO-$d_6$): δ 3.80 (s, 3H), 3.82 (s, 3H), 5.65 (s, 2H), 6.45 (dd, 1H), 6.55 (d, 1H), 7.00 (d, 1H), 7.35 (m, 1H), 7.55 (m, 1H), 7.75 (m, 2H), 7.90 (m, 1H), 8.22 (d, 1H).

E. 1-(2,4-Dimethoxybenzyl)-3-hydrazinobenzo[f]quinoxaline-2(1H)-one

A mixture of 3-chloro-1-(2,4-dimethoxybenzyl)benzo[f]quinoxalin-2(1H)-one (900 mg, 2.4 mmol) and hydrazine hydrate (250 μl, 5.1 mmol) in dichloromethane (70 ml) was stirred at room temperature. After 48 h the mixture was evaporated to dryness. The residue was triturated with ice/water, filtered and dried in vacuo to give 800 mg (85%) of the title compound. M.p. 182°–183° C., $^1$H-NMR (CDCl$_3$): δ 3.80 (s, 3H), 3.85 (s, 3H), 4,15 (br. s, 2H), 5.58 (s, 2H), 6.45 (dd, 1H), 6.58 (d, 1H), 7.05 (d, 1H), 7.40 (m, 3H), 7.70 (s, 2H), 7.85 (dd, 1H), 8.10 (d, 1H).

F. 3-(2-(Diethoxyphosphorylacetyl)hydrazino)-1-(2,4-dimethoxybenzyl)benzo[f]quinoxalin-2(1H)-one A solution of (diethoxyphosphoryl)acetyl chloride (480 mg, 2.2 mmol) in dry tetrahydrofuran (10 ml) was added to a mixture of 1-(2,4-dimethoxybenzyl)-3-hydrazinobenzo[f]quinoxalin-2(1H)-one (750 mg, 2 mmol) and dry triethylamine (220 mg, 2.2 mmol) in dry tetrahydrofuran (40 ml). The mixture was stirred at room temperature for 1.5 h and filtered. The filtrate was evaporated to give 1.1 g of the title compound as a crude product.

G. 3-[(Diethoxyphosphoryl)methyl]benzo[f]-1,2,4-triazolo[4,3-a]quinoxalin-12(11H)-one A solution of 3-(2-diethoxyphosphorylacetyl)hydrazino-1-(2,4-dimethoxybenzyl)benzo[f]quinoxalin-2(1H)-one (1.1 g crude product) and glacial acetic acid (40 ml) was heated under reflux for 12 h. The mixture was evaporated to dryness. The residue was recrystallized from isopropanol to give 400 mg of the title compound m.p. 195°–197° C. $^1$H-NMR (DMSO-d$_6$): δ 1.18 (t, 6H), 4.08 (quint, 4H), 4.35 (d, 2H), 7.68 (m, 2H), 7.90 (d, 1H), 8.08 (m, 1H), 8.35 (d, 1H), 8.82 (m, 1H), 12.25 (s, 1H).

EXAMPLE 19

1-[(Diethoxyphosphoryl)methyl]-8-trifluoromethyl[1,2,4]triazolo[4,3-a]quinoxalin-4(5H)-one This compound was prepared by the procedure described in example 18 starting from 4-fluoro-3-nitrobenzotrifluoride and 2,4-dimethoxybenzylamine, except that the intermediate 1-[(diethoxyphosphoryl)methyl]-5-(2,4-dimethoxybenzyl)-8-trifluoromethyl[1,2,4]triazolo[4,3-a]quinoxalin-4(5H)-one was deprotected by treatment with trifluoroacetic acid at room temperature overnight. The mixture was evaporated to dryness and the residue was recrystallized from ethanol to give the pure title compound, m.p. 204°–208° C.

$^1$H-NMR (DMSO-d$_6$): δ 1.17 (t, 6H), 4.06 (quint, 4H), 4.34 (d, 2H), 7.57 (d, 1H), 7.86 (d, 1H), 8.44 (s, 1H), 12.42 (s, 1H).

EXAMPLE 20

1-Phosphonomethyl-7-trifluoromethyl[1,2,4]triazolo[4,3-a]quinoxalin-4(5H)-one

Bromotrimethylsilane (0.75 ml, 5.8 mmol) was added to a suspension of 1-[(diethoxyphosphoryl)methyl]-7-trifluoromethyl[1,2,4]triazolo[4,3-a]quinoxalin-4(5H)-one (315 mg, 0.78 mmol) in 15 ml of dry acetonitrile in a flame-dried flask under nitrogen, and the resulting solution was stirred overnight at 40° C. After evaporation to dryness, the residue was stirred with 25 ml of water for 1 h. Then the water was removed under reduced pressure by azeotropic distillation with 1-propanol, and the residue was crystallized by trituration with a mixture of ether and ethanol followed by light petroleum. The solid was recrystallized from water, and dried in vacuo to give 189 mg (70%) of the title compound, m.p.>290° C. dec. (DSC); $^1$H-NMR (DMSO-d$_6$): δ 3.96 (d, 2H), 7.64 (d, 1H), 7.69 (s, 1H), 8.47 (d, 1H), 12.28 (s, 1H); IR (KBr): 1712 cm$^{-1}$; MS (FAB): m/e 349 (MH$^+$).

($C_{11}H_8N_4F_3O_4P.H_2O$) Calc.: C 36.08, H 2.75, N 15.30 Found: C 35.97, H 2.77, N 15.22

The compounds of the following examples were prepared in an analogous manner from the appropriate diethylphosphonates.

EXAMPLE 21

1-(2-Phosphonoethyl)-7-trifluoromethyl[1,2,4]triazolo[4,3-a]quinoxalin-4(5H)-one M.p.>300° C.; $^1$H-NMR (DMSO-d$_6$): δ 2.08–2.35 (m, 2H), 3.42–3.64 (m, 2H), 7.68 (d, 1H), 7.72 (s, 1H), 8.14 (d, 1H), 12.26 (br s, 1H);

MS (FAB): m/e 363 (MH$^+$).

($Cl_2H_{10}N_4F_3O_4P$) Calc.: C 39.78, H 2.76, N 15.47 Found: C 39.68, H 2.73, N 15.34

EXAMPLE 22

7-Cyano-1-phosphonomethyl-8-trifluoromethyl[1,2,4]triazolo[4,3-a]quinoxalin-4(5H)-one M.p.>255° C. decomp.; $^1$H-NMR (DMSO-d$_6$): δ 4.01 (d, 2H), 7.91 (s, 1H), 8.77 (s, 1H), 12.66 (s, 1H); IR (KBr): 2246, 1719 cm$^{-1}$; MS (FAB): m/e 374 (MH$^+$).

($C_{12}H_7N_5F_3O_4P.H_2O$) Calc.: C 36.84, H 2.32, N 17.90 Found: C 36.56, H 2.39, N 17.70

EXAMPLE 23

7-Cyano-1-phosphonomethyl[1,2,4]triazolo[4,3-a]quinoxalin-4(5H)-one

M.p.>275° C. decomp.; $^1$H-NMR (DMSO-d$_6$): δ 3.94 (d, 2H), 7.70 (s, 1H), 7.75 (d, 1H), 8.40 (d, 1H), 12.32 (br s, 1H); IR (KBr): 2242, 1720 cm$^{-1}$; MS (FAB): m/e 306 (MH$^+$).

($C_{11}H_8N_5O_4P.2.25 H_2O$) Calc.: C 38.22, H 3.64, N 20.26 Found: C 38.23, H 3.57, N 20.12

EXAMPLE 24

1-(1-Phosphonoethyl)-7-trifluoromethyl[1,2,4]triazolo[4,3-a]quinoxalin-4(5H)-one M.p.>300° C. decomp.; $^1$H-NMR (DMSO-d$_6$): δ 1.75 (dd, 3H), 4.27 (dq, 1H), 7.61 (d, 1H), 7.69 (s, 1H), 8.47 (d, 1H), 12.28 (s, 1H); MS (FAB): m/e 363 (MH$^+$).

($C_{12}H_{10}N_4F_3O_4P.0.25 H_2O$) Calc.: C 39.30, H 2.89, N 15.28 Found: C 39.33, H 2.84, N 14.91

EXAMPLE 25

8-Chloro-1-phosphonomethyl[1,2,4]triazolo[4,3-a]quinoxalin-4(5H)-one

M.p.>250 decomp.; $^1$H-NMR (DMSO-d$_6$): δ 3.93 (d, 2H), 7.39 (d, 1H), 7.55 (dd, 1H), 8.31 (d, 1H), 12.19 (s, 1H); MS (FAB): m/e 315 (MH$^+$).

($C_{10}H_8N_4Cl O_4P.0.5 H_2O$) Calc.: C 37.11, H 2.80, N 17.31 Found: C 36.84, H 2.97, N 17.15

EXAMPLE 26

8-Nitro-1-phosphonomethyl-7-trifluoromethyl[1,2,4]triazolo[4,3-a]quinoxalin-4(5H)-one M.p. 245°–248° C. $^1$H-NMR (DMSO-d$_6$): δ 4.00 (d, 2H), 7.89 (s, 1H), 9.04 (s, 1H), 12.65 (br s, 1H); MS (FAB): m/e 394 (MH$^+$).

($C_{11}H_7N_5F_3O_6P.0.5 H_2O$) Calc.: C 32.85, H 2.01, N 17.41 Found: C 32.94, H 2.01, N 17.11

EXAMPLE 27

1-Phosphonomethyl-8-trifluoromethyl[1,2,4]triazolo[4,3-a]quinoxalin-4(5H)-one

M.p. 282°–284° C. $^1$H-NMR (DMSO-d$_6$): δ 3.95 (d, 2H), 7.57 (d, 1H), 7.85 (d, 1H), 8.59 (s, 1H), 12.39 (s, 1H).

($C_{11}H_8N_4F_3O_4P.1 H_2O$) Calc.: C 36.08, H 2.75, N 15.30 Found: C 36.32, H 2.68, N 15.03

EXAMPLE 28

7-Nitro-1-phosphonomethyl[1,2,4]triazolo[4,3-a]quinoxalin-4(5H)-one

M.p.>265° C. decomp.; $^1$H-NMR (DMSO-$d_6$): δ 3.98 (d, 2H), 8.08 (dd, 1H), 8.22 (d, 1H), 8.49 (d, 1H), 12.40 (s, 1H); MS (FAB): m/e 326 (MH$^+$).

EXAMPLE 29

1-(1-Phosphonopropyl)-7-trifluoromethyl[1,2,4]triazolo[4,3-a]quinoxalin-4(5H)-one M.p.>240° C. decomp. (from ether/ethanol); $^1$H-NMR (DMSO-$d_6$): δ 0.95 (t, 3H), 2.08–2.61 (m, 2H), 3.95–4.15 (m, 1H), 7.62 (d, 1H), 7.69 (s, 1H), 8.50 (d 1H), 12.28 (s, 1H).

($C_{13}H_{12}N_4F_3O_4P$.0.5 $H_2O$.0.25 $C_2H_5OH$) Calc.: C 40.87, H 3.68, N 14.12 Found: C 40.81, H 3.80, N 13.95

EXAMPLE 30

3-Phosphonomethylbenzo[f]-1,2,4-triazolo[4,3-a]quinoxalin-12(11H)-one

M.p.>270° C.; $^1$H-NMR (DMSO-$d_6$): δ 4.02 (d, 2H), 7.65 (m, 2H), 7.85 (m, 1H), 8.05 (m, 1H), 8.40 (m, 1H), 8.80 (m, 1H), 12.15 (s, 1H).

EXAMPLE 31

1-[(Ethoxyhydroxyphosphoryl)methyl]-7-trifluoromethyl[1,2,4]triazolo[4,3-a]quinoxalin-4(5H)-one A solution of 1-[(diethoxyphosphoryl)methyl]-7-trifluoromethyl[1,2,4]triazolo[4,3-a]quinoxalin-4 (5H)-one (750 mg, 1.85 mmol) in 20 ml of ethanol and 20 ml of 10% sodium hydroxide was stirred at room temperature for 1 h. The solvent was removed under reduced pressure, and the residue was dissolved in water and applied to an ion-exchange column (Amberlite IR-120, H$^+$-form) prewashed with 4M hydrochloric acid followed by deionized water. Elution with deionized water gave an acidic eluate, which was concentrated in vacuo to give 448 mg (65%) of the title compound, m.p. 276°–280° C. (from water); $^1$H-NMR (DMSO-$d_6$): δ 1.16 (t, 3H), 3.98 (quint, 2H), 4.08 (d, 2H), 7.64 (d, 1H), 7.68 (s, 1H), 8.42 (d, 1H), 12.28 (s, 1H), MS: m/e 377 (MH$^+$).

EXAMPLE 32

8-Bromo-1-[1-(diethoxyphosphoryl)ethyl]-7-trifluoromethyl[1,2,4]triazolo[4,3-a]quinoxalin-4(5H)-one A mixture of 1-[1-(diethoxyphosphoryl)ethyl]-7-trifluoromethyl[1,2,4]triazolo[4,3-a]quinoxalin-4(5H)-one (811 mg, 1.94 mmol), silver sulfate (605 mg, 1.94 mmol) and bromine (100 μl, 1.94 mmol) in 5 ml of conc. sulfuric acid was stirred overnight at room temperature. The mixture was filtered and the filtrate was added dropwise to 100 ml of ice/water. The resulting precipitate was isolated by filtration, washed with water and dried to give 514 mg (53%) of the title compound; m.p.>200° C., decomp. $^1$H-NMR (DMSO-$d_6$): δ 1.12 (t, 3H), 1.18 (t, 3H), 1.74 (dd, 3H), 3.95 (quint, 2H), 4.07 (quint, 2H), 4.78 (dq, 1H), 7.81 (s, 1H), 8.59 (s, 1H), 12.35 (s, 1H).

EXAMPLE 33

8-Bromo-1-(1-phosphonoethyl)-7-trifluoromethyl[1,2,4]triazolo[4,3-a]quinoxalin-4 (5H)-one The title compound was prepared from 8-bromo-1-[1-(diethoxyphosphoryl)ethyl]-7-trifluoromethyl[1,2,4]triazolo[4,3-a]quinoxalin-4(5H)-one by the method described in example 20. M.p.>300° C.; $^1$H-NMR (DMSO-$d_6$): δ 1.66 (distorted dd, 3H), 3.87 (distorted dq, 1H), 7.76 (s, 1H), 8.80 (s, 1H), 12.3 (br. s, 1H); MS (FAB): m/e 441, 443 (MH$^+$).

($C_{13}H_9N_5F_3O_4P$.1.5 $H_2O$) Calc.: C 30.79 H 2.58 N 11.97 Found: C 30.42 H 2.30 N 11.90

I claim:

1. A compound of formula I

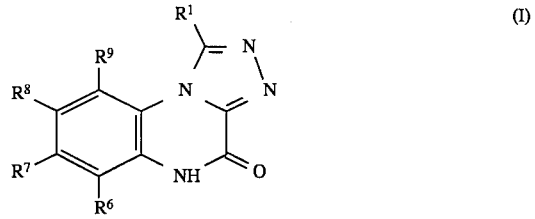

wherein $R^1$ is COX', POX'X" or straight or branched $C_{1-6}$-alkyl substituted with COX' or POX'X", wherein X' and X" independently are hydroxy or $C_{1-6}$-alkoxy; and $R^6$ and $R^7$ or $R^8$ and $R^9$ form a fused benzene or tetrahydro-benzene ring; or a pharmaceutically acceptable salt thereof.

2. A compound according to claim 1, wherein $R^6$ and $R^7$ or $R^8$ and $R^9$ form a fused benzene ring.

3. A compound according to claim 2 which is

3-[(Diethoxyphosphoryl)methyl]benzo[f]-1,2,4-triazolo[4,3-a]quinoxalin-12(11H)-one;

3-Phosphonomethylbenzo[f]-1,2,4-triazolo[4,3-a]quinoxalin-12(11H)-one; or a pharmaceutically acceptable salt thereof.

4. A pharmaceutical composition comprising a compound according to claim 1 and a pharmaceutically acceptable carrier or diluent.

5. A pharmaceutical composition according to claim 4 in the form of a dosage unit containing about 10–200 mg of the active compound.

6. A compound of formula I

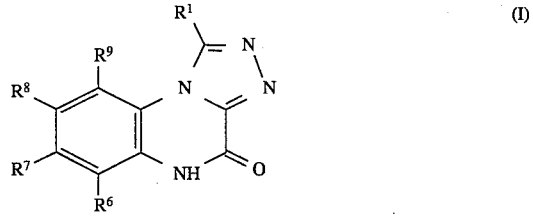

wherein $R^1$ is POX'X" or straight or branched $C_{1-6}$-alkyl substituted with POX'X", wherein X' and X" independently are hydroxy or $C_{1-6}$-alkoxy; and $R^6$, $R^7$, $R^8$, and $R^9$ independently are hydrogen; $C_{1-6}$-alkyl; halogen; $NH_2$; $NO_2$; CN; $CF_3$; triazolyl; imidazolyl; imidazolyl substituted with phenyl or $C_{1-6}$-alkyl; $SO_2NY'Y"$; or COZ' wherein Z' is NY'Y" or $C_{1-6}$-alkyl; wherein Y' and Y" independently are hydrogen or $C_{1-6}$-alkyl; or a pharmaceutically acceptable salt thereof.

7. A compound according to claim 6 which is

1-[(Diethoxyphosphoryl)methyl]-7-trifluoromethyl[1,2,4]triazolo[4,3 -a]quinoxalin-4(5H)-one;

7-Cyano-1-[(diethoxyphosphoryl)methyl]-8-trifluoromethyl[1,2,4]triazolo[4,3 -a]quinoxalin-4(5H)-one;

7-Cyano-1-[(diethoxyphosphoryl)methyl][1,2,4]triazolo[4,3-a]quinoxalin-4(5H)-one;

8-Chloro-1-[(diethoxyphosphoryl)methyl][1,2,4]triazolo[4,3-a]quinoxalin-4(5H)-one;

1-[(Diethoxyphosphoryl)methyl]-7-nitro[1,2,4]triazolo[4,3-a]quinoxalin-4(5H)-one;

1-[(Diethoxyphosphoryl)methyl]-8-nitro-7-trifluoromethyl[1,2,4]triazolo[4,3 -a]quinoxalin-4(5H)-one;

8-Amino-1-[(diethoxyphosphoryl)methyl]-7-trifluoromethyl[1,2,4]triazolo[4,3 -a]quinoxalin-4(5H)-one;

1-[(Diethoxyphosphoryl)methyl]-8-trifluoromethyl[1,2,4]triazolo[4,3-a]quinoxalin-4(5H)-one; or a pharmaceutically acceptable salt thereof.

8. A compound according to claim 6 which is

1-[2-(Diethoxyphosphoryl)ethyl]-7-trifluoromethyl[1,2,4]triazolo[4,3 -a]quinoxalin-4(5H)-one; or a pharmaceutically acceptable salt thereof.

9. A compound according to claim 6 which is

1-[1-(Diethoxyphosphoryl)ethyl]-7-trifluoromethyl[1,2,4]triazolo[4,3 -a]quinoxalin-4(5H)-one;

8-Bromo-1-[1-(diethoxyphosphoryl)ethyl]-7-trifluoromethyl[1,2,4]triazolo[4,3 -quinoxalin-4(5H)-one; or a pharmaceutically acceptable salt thereof.

10. A compound according to claim 6 which is

1-[1-(Diethoxyphosphoryl)propyl]-7-trifluoromethyl[1,2,4]triazolo[4,3 -a]quinoxalin-4(5H)-one; or a pharmaceutically acceptable salt thereof.

11. A compound according to claim 6 which is

1-Phosphonomethyl-7-trifluoromethyl[1,2,4]triazolo[4,3-a]quinoxalin-4(5H)-one;

7-Cyano-1-phosphonomethyl-8-trifluoromethyl[1,2,4]triazolo[4,3-a]quinoxalin-4(5H)-one;

7-Cyano-1-phosphonomethyl[1,2,4]triazolo[4,3-a]quinoxalin-4(5H)-one;

8-Chloro-1-Phosphonomethyl[1,2,4]triazolo[4,3-a]quinoxalin-4(5H)-one;

8-Nitro-1-phosphonomethyl-7-trifluoromethyl[1,2,4]triazolo[4,3-a]quinoxalin-(5H)-one;

1-Phosphonomethyl-8-trifluoromethyl[1,2,4]triazolo[4,3-a]quinoxalin-4(5H)-one;

7-Nitro-1-phosphonomethyl[1,2,4]triazolo[4,3-a]quinoxalin-4(5H)-one; or a pharmaceutically acceptable salt thereof.

12. A compound according to claim 6 which is 1-(2-Phosphonoethyl)-7-trifluoromethyl[1,2,4]triazolo[4,3-a]quinoxalin-4(5H)-one; or a pharmaceutically acceptable salt thereof.

13. A compound according to claim 6 which is 1-(1-Phosphonoethyl)-7-trifluoromethyl[1,2,4]triazolo[4,3-a]quinoxalin-4(5H)-one;

8-Bromo-1-[1-(phosphonoethyl)-7-trifluoromethyl[1,2,4]triazolo[4,3-1]quinoxalin-4(5H)-one; or a pharmaceutically acceptable salt thereof.

14. A compound according to claim 6 which is 1-(1-Phosphonopropyl)-7-trifluoromethyl[1,2,4]triazolo[4,3-a]quinoxalin-4(5H)-one; or a pharmaceutically acceptable salt thereof.

15. A compound according to claim 6 which is

1-[(Ethoxyhydroxyphosphoryl)methyl]-7-trifluoromethyl[1,2,4]triazolo[4,3 -a]quinoxalin-4(5H)-one; or a pharmaceutically acceptable salt thereof.

16. A pharmaceutical composition comprising a compound according to claim 6 and a pharmaceutically acceptable carrier or diluent.

17. A pharmaceutical composition according to claim 16 in the form of a dosage unit containing about 10–200 mg of the active compound.

18. A compound of formula I wherein $R^1$ is COOH or straight or branched $C_{1-6}$-alkyl substituted with COX', wherein X' is hydroxy or $C_{1-6}$-alkoxy; and $R^6$, $R^7$, $R^8$, and $R^9$ independently are hydrogen; $C_{1-6}$-alkyl; halogen; $NH_2$; $NO_2$; CN; $CF_3$; triazolyl; imidazolyl; imidazolyl substituted with phenyl or $C_{1-6}$-alkyl; $SO_2NY'Y''$; or COZ' wherein Z' is NY'Y'' or $C_{1-6}$-alkyl; wherein Y' and Y'' independently are hydrogen or $C_{1-6}$-alkyl; or a pharmaceutically acceptable salt thereof.

19. A compound according to claim 18 which is 1-(2-Ethoxycarbonylethyl)-7-nitro[1,2,4]triazolo[4,3-a]quinoxalin-4(5H)-one;

7-Cyano-1-(2-ethoxycarbonylethyl)-8-trifluoromethyl[1,2,4]triazolo[4,3 -a]quinoxalin-4(5H)-one;

1-(2-Ethoxycarbonylethyl)-7-trifluoromethyl[1,2,4]triazolo[4,3-a]quinoxalin-4(5H)-one; or a pharmaceutically acceptable salt thereof.

20. A compound according to claim 18 which is 1-(2-Carboxyethyl)-7-nitro[1,2,4]triazolo[4,3-a]quinoxalin-4(5H)-one;

7-Carbamoyl-1-(2-carboxyethyl)-8-trifluoromethyl[1,2,4]triazolo[4,3-a]quinoxalin-4 (5H)-one;

1-(2-Carboxyethyl)-7-cyano-8-trifluoromethyl[1,2,4]triazolo[4,3-a]quinoxalin-4(5 H)-one;

1-(2-Carboxyethyl-7-trifluoromethyl[1,2,4]triazolo[4,3-a]quinoxalin-4(5H)-one;

or a pharmaceutically acceptable salt thereof.

21. A pharmaceutical composition comprising a compound according to claim 18 and a pharmaceutically acceptable carrier or diluent.

22. A pharmaceutical composition according to claim 21 in the form of a dosage unit containing about 10–200 mg of the active compound.

23. A method of treating an indication, comprising administering a compound to a subject in need thereof, wherein the compound is of formula I:

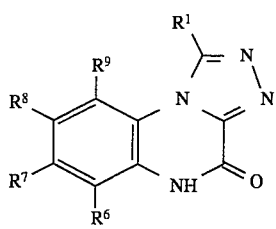 (I)

wherein
- $R^1$ is COX', POX'X" or straight or branched $C_{1-6}$-alkyl substituted with COX' or POX'X", wherein X' and X" independently are hydroxy or $C_{1-6}$-alkoxy; and
- $R^6$, $R^7$, $R^8$, and $R^9$ independently are hydrogen; $C_{1-6}$-alkyl; halogen; $NH_2$; $NO_2$; CN; $CF_3$; triazolyl; imidazolyl; imidazolyl substituted with phenyl or $C_{1-6}$-alkyl; $SO_2NY'Y"$; or COZ' wherein Z' is NY'Y" or $C_{1-6}$-alkyl; wherein Y' and Y" independently are hydrogen or $C_{1-6}$-alkyl; or $R^6$ and $R^7$ or $R^8$ and $R^9$ form a fused benzene or tetrahydro-benzene ring; or a pharmaceutically acceptable salt thereof, wherein the indication is cerebral ischemia or Parkinson's disease.

24. A method according to claim 23, wherein the indication is cerebral ischemia.

25. A method according to claim 23, wherein the indication is Parkinson's disease.

* * * * *